United States Patent
Ichimasa (10) Patent No.: US 9,212,592 B2
(45) Date of Patent: Dec. 15, 2015

(54) EXHAUST SENSOR (75) Inventor: Toshio Ichimasa, Fujisawa (JP)

(73) Assignee: Isuzu Motors Limited, Tokyo (JP)

( * ) Notice: Subject to any disclaimer, the term of this patent is extended or adjusted under 35 U.S.C. 154(b) by 248 days.

(21) Appl. No.: 13/640,938

(22) PCT Filed: Apr. 11, 2011

(86) PCT No.: PCT/JP2011/058994
§ 371 (c)(1),
(2), (4) Date: Oct. 12, 2012

(87) PCT Pub. No.: WO2011/129296
PCT Pub. Date: Oct. 20, 2011

(65) Prior Publication Data
US 2013/0031967 A1    Feb. 7, 2013

(30) Foreign Application Priority Data

Apr. 15, 2010  (JP) ................... 2010-094340

(51) Int. Cl.
*F01N 13/00* (2010.01)
*F01N 11/00* (2006.01)
(Continued)

(52) U.S. Cl.
CPC .............. *F01N 13/008* (2013.01); *F01N 11/00* (2013.01); *F02D 41/1466* (2013.01);
(Continued)

(58) Field of Classification Search
CPC .. G01N 1/2252; G01N 15/0656; F01N 3/021; F01N 3/031; F01N 11/00; F01N 13/008; F01N 2340/06; F01N 2560/02; F02D 41/1466; F02B 37/00

USPC ............... 73/23.2, 23.31, 31.02, 31.03, 31.05
See application file for complete search history.

(56) References Cited

U.S. PATENT DOCUMENTS 3,607,084 A * 9/1971 Mackey et al. ............... 436/152
3,766,715 A * 10/1973 Archer ............................. 95/279
(Continued)

FOREIGN PATENT DOCUMENTS

JP       52-13584       4/1977
JP       63-96218       6/1988
(Continued)

OTHER PUBLICATIONS

A Search Report issued in corresponding International Appln. No. PCT/JP2011/058994 dated Jul. 12, 2011 (4 pages).
(Continued)

*Primary Examiner* — Daniel S Larkin
(74) *Attorney, Agent, or Firm* — McCormick, Paulding & Huber LLP (57) ABSTRACT

An exhaust sensor (10) includes a cylindrical sensor body (11) arranged outside of an exhaust pipe (5) of an engine (1), a gas inlet (12) formed at one end of sensor body (11), and a gas outlet (13) formed at the other end of sensor body (11). The gas inlet (12) communicates with the exhaust pipe (5) through an introduction pipe (16), while the gas outlet (13) communicates, through a return pipe (17), with the exhaust pipe (5) on the downstream side of a communication portion (16a) of the introduction pipe (16) in terms of flow of the exhaust gas, and the exhaust gas is introduced into the sensor body (11) through the gas inlet (12) and then discharged from the sensor body (11) through the gas outlet (13) by a pressure difference between the communication portions (16a), (17a) of the introduction pipe (16) and of the return pipe (17).

10 Claims, 10 Drawing Sheets

(51) Int. Cl.
- *F02D 41/14* (2006.01)
- *G01N 1/22* (2006.01)
- *F01N 3/021* (2006.01)
- *F01N 3/031* (2006.01)
- *F02B 37/00* (2006.01)
- *G01N 15/06* (2006.01)

(52) U.S. Cl.
CPC ............ *G01N 1/2252* (2013.01); *F01N 3/021* (2013.01); *F01N 3/031* (2013.01); *F01N 2340/06* (2013.01); *F01N 2560/02* (2013.01); *F02B 37/00* (2013.01); *G01N 15/0656* (2013.01); *Y02T 10/47* (2013.01)

(56) References Cited

U.S. PATENT DOCUMENTS

| | | | |
|---|---|---|---|
| 5,105,619 A * | 4/1992 | Arai | 60/286 |
| 5,711,148 A | 1/1998 | Katoh | |
| 5,836,155 A | 11/1998 | Katoh | |
| 7,739,898 B2 * | 6/2010 | Shaddock et al. | 73/31.05 |
| 2009/0084097 A1 | 4/2009 | Sato et al. | |
| 2010/0132336 A1 * | 6/2010 | Tsujimoto | 60/286 |
| 2013/0047841 A1 | 2/2013 | Zidat | |

FOREIGN PATENT DOCUMENTS

| | | |
|---|---|---|
| JP | 3-1235 U | 1/1991 |
| JP | 3-74549 A | 3/1991 |
| JP | 7-301135 A | 11/1995 |
| JP | 2004198121 A | 7/2004 |
| WO | 2009/109688 A1 | 9/2009 |
| WO | 2011032933 A1 | 3/2011 |

OTHER PUBLICATIONS

European Search Report for European Patent Application No. EP11768817.6 dated Sep. 18, 2014.

* cited by examiner

EXHAUST SENSOR

CROSS REFERENCE TO RELATED APPLICATIONS

This application is entitled to the benefit of and incorporates by reference essential subject matter disclosed in International Patent Application No. PCT/JP2011/058994 filed on Apr. 11, 2011 and Japanese Patent Application No. 2010-094340 filed on Apr. 15, 2010.

TECHNICAL FIELD

This invention relates to an exhaust sensor for measuring exhaust gas components.

BACKGROUND ART

An exhaust sensor is arranged, for example, in an engine exhaust pipe downstream of an exhaust gas post-treatment apparatus in terms of flow of exhaust gas to measure exhaust gas components. The exhaust gas post-treatment apparatus may be, for example, a diesel particulate filter (DPF) for collecting particulate matters (PM) contained in the exhaust gas, and the exhaust sensor may be, for example, a PM sensor for detecting an emission of particulate matters (PM).

One prior art document is WO2009/109688.

DISCLOSURE OF THE INVENTION

In order to introduce exhaust gas into the inside (sensing portion) of an exhaust sensor, it is proposed to arrange an exhaust sensor (sensor body) in the inside of the engine exhaust pipe. In this case, the exhaust sensor itself will become a resistance against flow of the exhaust gas within the exhaust pipe, causing increase in engine back pressure, and possibly leading to deterioration of fuel economy of the engine.

Therefore, an object of the invention is to prevent the deterioration of engine fuel economy by suppressing increase in engine back pressure caused by attachment of an exhaust sensor.

In order to achieve the aforementioned object, the invention provides an exhaust sensor for measuring exhaust gas components, including: a cylindrical sensor body arranged outside of an exhaust pipe of an engine; a gas inlet formed at one end of the sensor body; and a gas outlet formed at the other end of the sensor body. The gas inlet communicates with the exhaust pipe through an introduction pipe, while the gas outlet communicates, through a return pipe, with the exhaust pipe on the downstream side of a communication portion of the introduction pipe in terms of flow of the exhaust gas. Thus, the exhaust gas is introduced into the sensor body through the gas inlet and then discharged from the sensor body through the gas outlet by a pressure difference between the communication portion of the introduction pipe and a communication portion of the return pipe.

An open/close valve may be provided in either one or both of the introduction pipe and the return pipe.

A turbine may be provided in the exhaust pipe, and the introduction pipe and the return pipe may be connected to the exhaust pipe on the downstream side of the turbine in terms of flow of the exhaust gas.

An exhaust gas post-treatment apparatus may be provided in the exhaust pipe on the downstream side of the turbine in terms of flow of the exhaust gas, and the introduction pipe and the return pipe may be connected to the exhaust pipe on the downstream side of the exhaust gas post-treatment apparatus in terms of flow of the exhaust gas.

An exhaust gas post-treatment apparatus may be provided in the exhaust pipe on the downstream side of the turbine in terms of flow of the exhaust gas, and the introduction pipe and the return pipe may be connected to the exhaust pipe on the upstream side of the exhaust gas post-treatment apparatus in terms of flow of the exhaust gas.

An exhaust gas post-treatment apparatus may be provided in the exhaust pipe on the downstream side of the turbine in terms of flow of the exhaust gas, and the introduction pipe may be connected to the exhaust pipe on the upstream side of the exhaust gas post-treatment apparatus in terms of flow of the exhaust gas, while the return pipe may be connected to the exhaust pipe on the downstream side of the exhaust gas post-treatment apparatus in terms of flow of the exhaust gas.

A guide may be provided in the communication portion between the exhaust pipe and the introduction pipe for the purpose of efficient introduction of the exhaust gas into the sensor body.

The invention provides an excellent effect that deterioration of engine fuel economy can be prevented by suppressing the increase in engine back pressure caused by attachment of an exhaust sensor.

MODE FOR CARRYING OUT THE INVENTION

Preferred embodiments of the invention will be described in detail with reference to the accompanying drawings.

Figure 1:
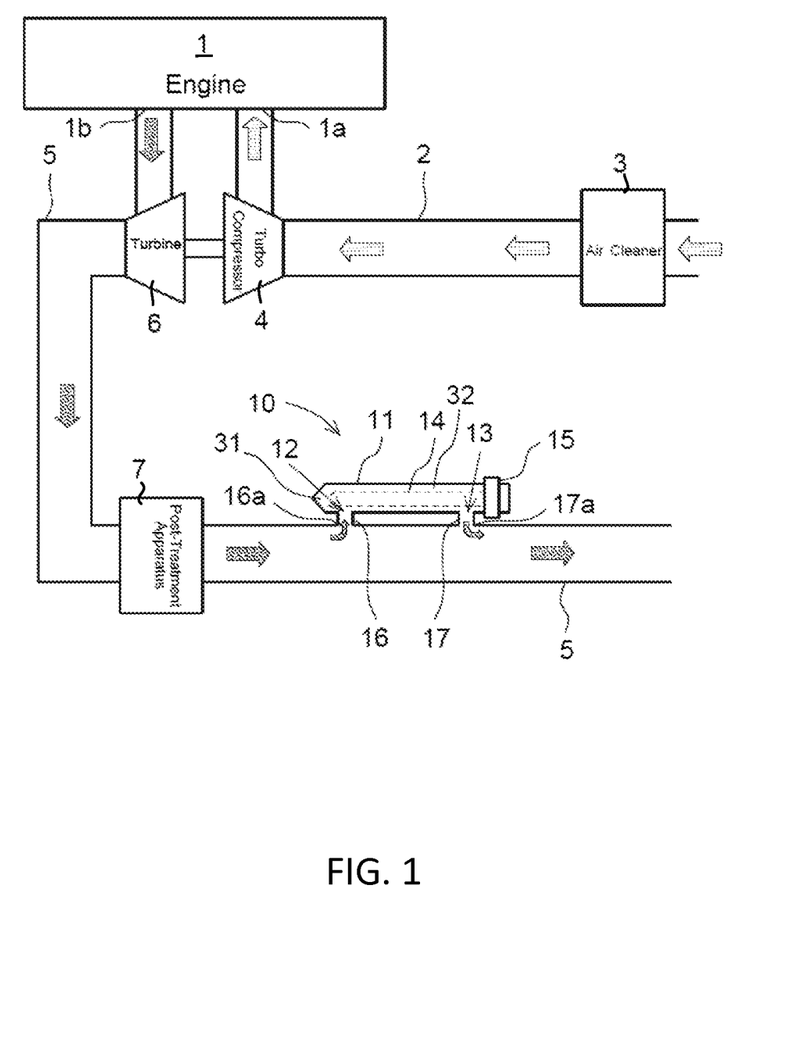
FIG. 1 is a schematic diagram showing an engine on which an exhaust sensor according to an embodiment of the invention is mounted.

In FIG. 1, the reference numeral 1 denotes an engine (diesel engine in this embodiment), 2 denotes an intake pipe connected to an intake port 1*a* of the engine 1, 3 denotes an air cleaner arranged in the intake pipe 2, 4 denotes a turbo compressor (turbo charger compressor) for pressurizing air supplied to the engine 1 and arranged in the intake pipe 2 downstream of the air cleaner 3 in terms of flow of intake air, 5 denotes an exhaust pipe (tail pipe) connected to an exhaust port 1b of the engine 1, 6 denotes a turbine for driving the turbo compressor 4 and arranged in the exhaust pipe 5, and 7 denotes an exhaust gas post-treatment apparatus arranged in the exhaust pipe 5 downstream of the turbine 6 in terms of flow of the exhaust gas. The exhaust gas post-treatment apparatus 7 has, for example, a diesel particulate filter (DPF) for collecting particulate matters (PM) contained in the exhaust gas.

The exhaust sensor 10 according to this embodiment is a sensor which is mounted on a vehicle and designed on the assumption that the vehicle has an on-board diagnostics (OBD) function. The exhaust sensor 10 is a PM sensor which electrically charges air supplied thereto at an electrode 31 and detects an emission of particulate matters (PM) trapped at an ion trap 32 based on a variation in electrical charge.

The exhaust sensor 10 according to this embodiment has a cylindrical (bottomed cylindrical or sheath-shaped) sensor body 11 arranged outside of the exhaust pipe 5 of the engine 1, a gas inlet 12 formed at one end of the sensor body 11, a gas outlet 13 formed at the other end of the sensor body 11, a nozzle 14 housed within the sensor body 11 and ejecting air from the front end thereof, an electrode 31 for electrically charging air, and a cover 15 for closing the other end of the sensor body 11.

In this embodiment, the sensor body 11 and the nozzle 14 are arranged concentrically with each other. Although not shown in the drawings, an air compressor is connected to the base end of the nozzle 14 so that air is supplied to the nozzle 14 by this air compressor.

Further, in this embodiment, the gas inlet 12 formed in the sensor body 11 communicates with the exhaust pipe 5 through an introduction pipe 16, and the gas outlet 13 formed in the sensor body 11 communicates, through a return pipe 17, with the exhaust pipe 5 on the downstream side of a communication portion 16a of the introduction pipe 16 in terms of flow of the exhaust gas.

In the embodiment, more particularly, one end of the introduction pipe 16 (an exhaust gas introduction portion, or the communication portion 16a of the introduction pipe 16 to the exhaust pipe 5) is connected to the exhaust pipe 5 on the downstream side of the exhaust gas post-treatment apparatus 7 in terms of flow of the exhaust gas, and the other end of the introduction pipe 16 is connected to the sensor body 11 (the gas inlet 12). One end of the return pipe 17 is connected to the sensor body 11 (the gas outlet 13), and the other end of the return pipe 17 (an exhaust gas return portion, or the communication portion 17a of the return pipe 17 to the exhaust pipe 5) is connected to the exhaust pipe 5 on the downstream side of the communication portion 16a of the introduction pipe 16 in terms of flow of the exhaust gas.

Operation of the embodiment will be described below.

In this embodiment, the sensor body 11 of the exhaust sensor 10 is arranged outside of the exhaust pipe 5 of the engine 1. Therefore, the exhaust sensor 10 (the sensor body 11) will not inhibit flow of the exhaust gas within the exhaust pipe 5. Since flow of the exhaust gas within the exhaust pipe 5 is not inhibited by the exhaust sensor 10, the attachment of the exhaust sensor 10 will not cause increase in back pressure of the engine 1, and hence the fuel economy of the engine 1 is not deteriorated.

In this embodiment, the gas inlet 12 communicates with the exhaust pipe 5 through the introduction pipe 16, while the gas outlet 13 communicates, through the return pipe 17, with the exhaust pipe 5 on the downstream side of the communication portion 16a of the introduction pipe 16 in terms of flow of the exhaust gas. Therefore, the exhaust gas is discharged from the gas outlet 13 after being introduced into the inside of the sensor body 11 through the gas inlet 12, and then is allowed to return smoothly into the inside of the exhaust pipe 5 by a pressure difference between the communication portion 16a of the introduction pipe 16 and the communication portion 17a of the return pipe 17.

In the conventional exhaust sensor shown in FIG. 1 of International Publication No. WO2009/109688, the exhaust sensor which is arranged within the exhaust pipe inhibits flow of the exhaust gas. In the exhaust sensor shown in FIG. 3 of International Publication No. WO2009/109688, an electrode (29) and an ion trap (9) are arranged in an axial direction instead of on a concentric circle. Consequently, the size of the exhaust sensor is increased. According to the invention, the exhaust sensor (of the type corresponding to the one shown in FIG. 1 of International Publication No. WO2009/109688) having an electrode (29) and an ion trap (9) arranged on a concentric circle is arranged outside of the exhaust pipe.

Although the invention has been described in its preferred form, it is understood that the invention is not limited to the embodiment described above, and various modifications and variations are possible.

Figure 2:
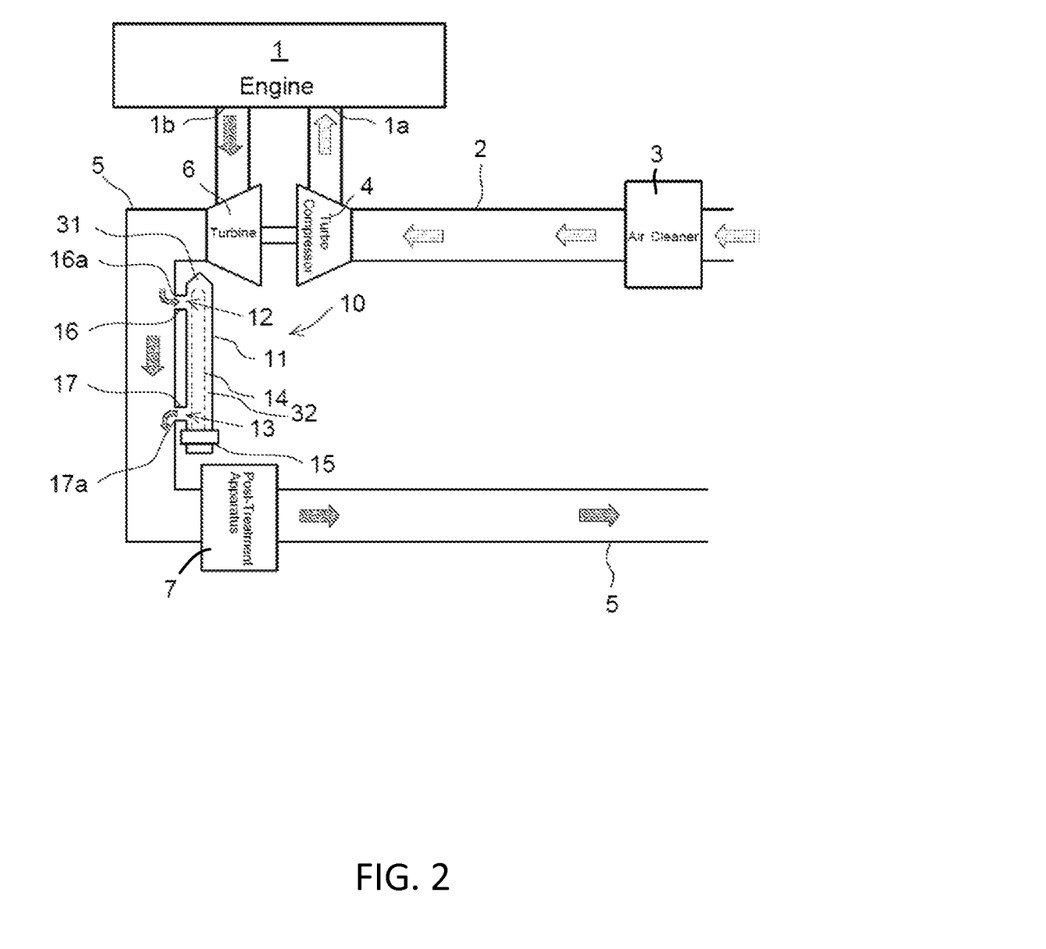
FIG. 2 is schematic diagram showing an engine on which an exhaust sensor according to another embodiment of the invention is mounted.

For example, in the embodiment described above, the exhaust gas introduction portion (the communication portion 16a of the introduction pipe 16 to the exhaust pipe 5) and the exhaust gas return portion (the communication portion 17a of the return pipe 17 to the exhaust pipe 5) are arranged in the exhaust pipe 5 on the downstream side of the exhaust gas post-treatment apparatus 7 in terms of flow of the exhaust gas. However, depending on characteristics of the exhaust sensor 10, as shown in FIG. 2, the exhaust gas introduction portion (the communication portion 16a of the introduction pipe 16 to the exhaust pipe 5) and the exhaust gas return portion (the communication portion 17a of the return pipe 17 to the exhaust pipe 5) can be arranged in the exhaust pipe 5 on the upstream side of the exhaust gas post-treatment apparatus 7 in terms of flow of the exhaust gas.

Figure 3:
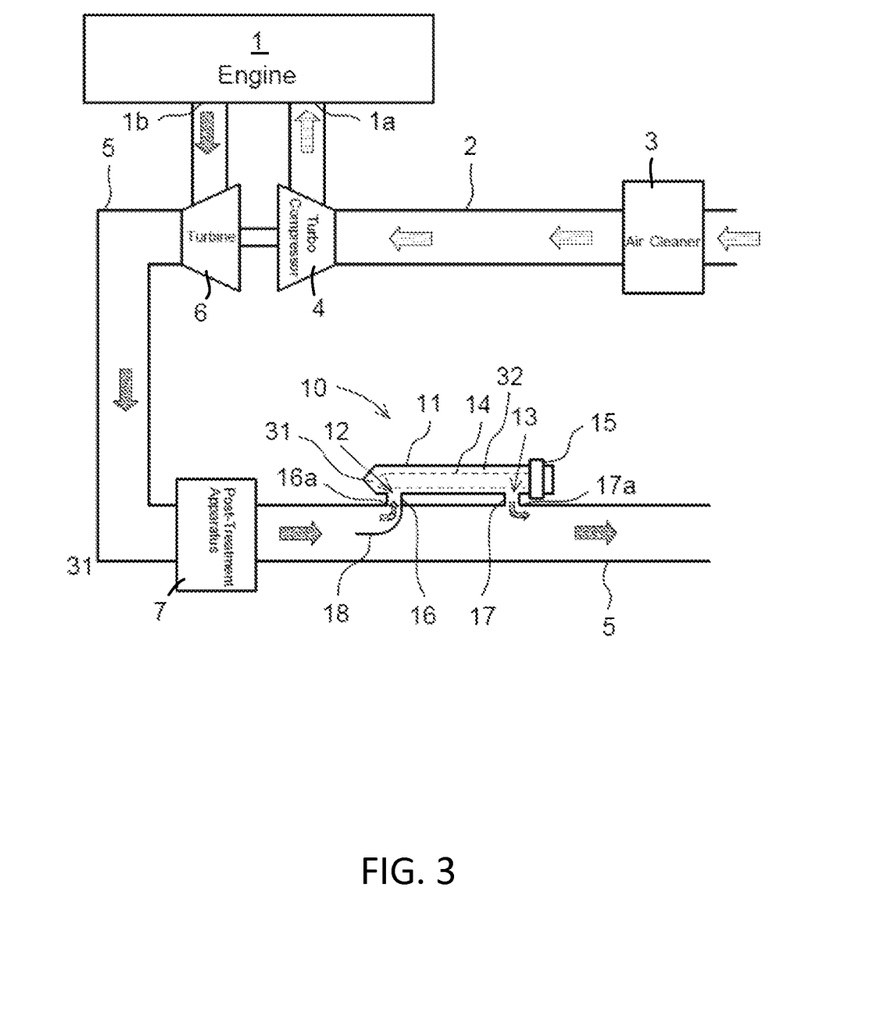
FIG. 3 is a schematic diagram showing an engine on which an exhaust sensor according to still another embodiment of the invention is mounted.

In order to enable efficient introduction and discharge of the exhaust gas into and from the inside of the sensor body 11, a guide 18 may be provided in the exhaust gas introduction portion (the communication portion 16a of the introduction pipe 16 to the exhaust pipe 5) as shown in FIG. 3.

Figure 4:
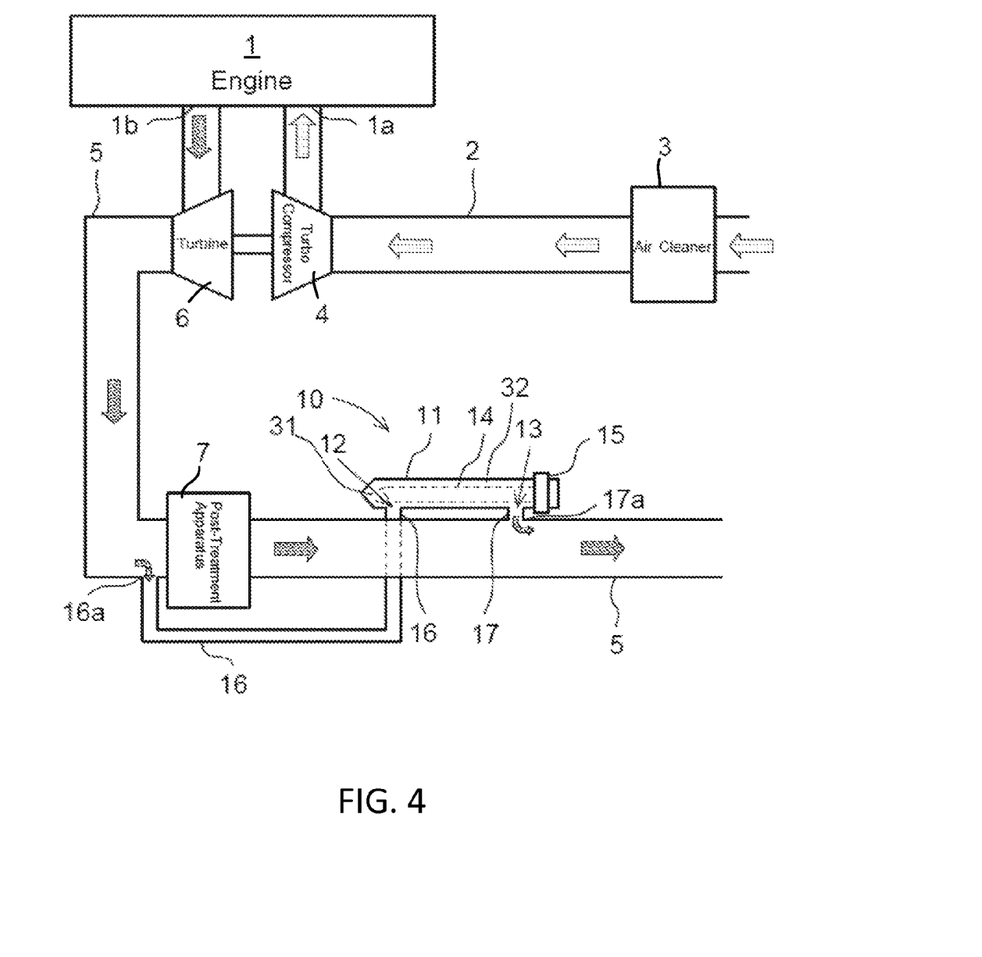
FIG. 4 is a schematic diagram showing an engine on which an exhaust sensor according to still another embodiment of the invention is mounted.

Further, in order to enable efficient introduction and discharge of the exhaust gas into and from the inside of the sensor body 11, the exhaust gas return portion (the communication portion 17a of the return pipe 17 to the exhaust pipe 5) may be arranged at a position where a pressure difference with the exhaust gas introduction portion (the communication portion 16a of the introduction pipe 16 to the exhaust pipe 5) is greater. For an example, as shown in FIG. 4, the exhaust gas introduction portion (the communication portion 16a of the introduction pipe 16 to the exhaust pipe 5) may be arranged in the exhaust pipe 5 upstream of the exhaust gas post-treatment apparatus 7 in terms of flow of the exhaust gas, and the exhaust gas return portion (the communication portion 17a of the return pipe 17 to the exhaust pipe 5) may be arranged in the exhaust pipe 5 on the downstream side of the exhaust gas post-treatment apparatus 7 in terms of flow of the exhaust gas.

Figure 5:
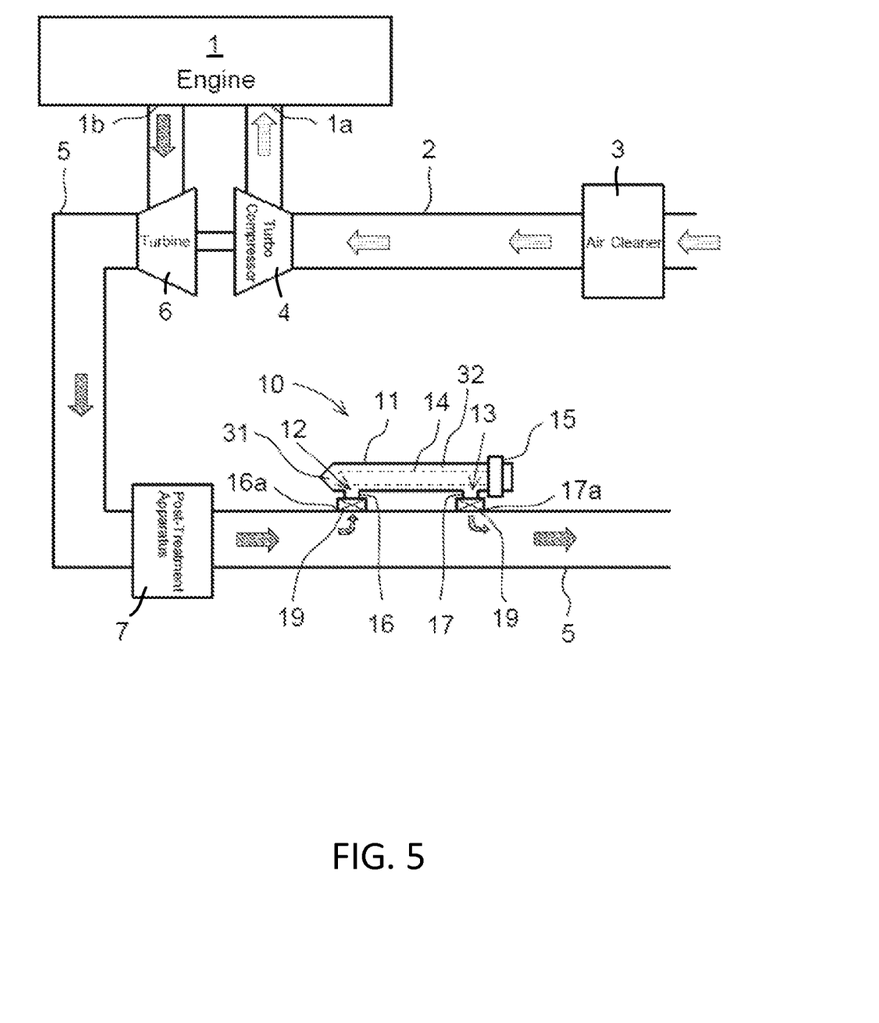
FIG. 5 is a schematic diagram showing an engine on which an exhaust sensor according to still another embodiment of the invention is mounted.

Further, as shown in FIG. 5, a valve (open/close valve) 19 may be provided in either one or both of the introduction pipe 16 and the return pipe 17 (more particularly, in either one or both of the communication portion 16a of the introduction pipe 16 and the communication portion 17a of the return pipe 17), so that the exhaust gas can be introduced into the inside of the exhaust sensor 10 (the inside of the sensor body 11)

only when the exhaust gas is required for sensing. In the example shown in FIG. 5, the valve 19 is provided in each of the introduction pipe 16 and the return pipe 17.

Figure 6:
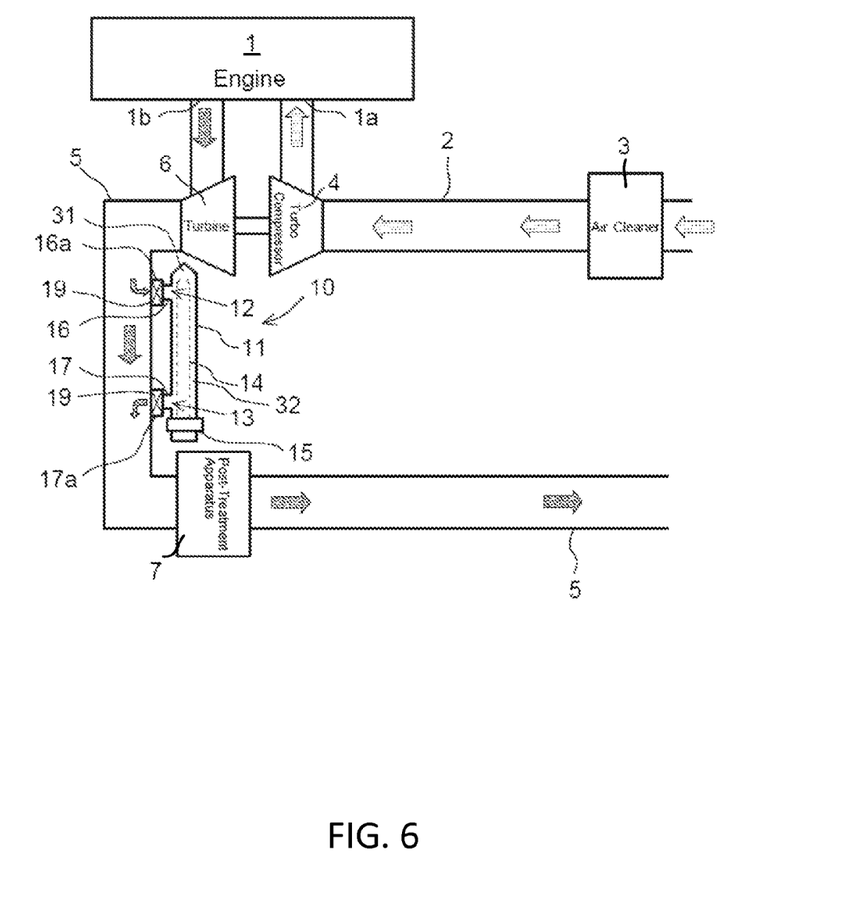
FIG. 6 is a schematic diagram showing an engine on which an exhaust sensor according to still another embodiment of the invention is mounted.

As shown in FIG. 6, a turbine 6 may be provided in the exhaust pipe 5, and the introduction pipe 16 and the return pipe 17 may be connected to the exhaust pipe 5 on the downstream side of the turbine 6 in terms of flow of the exhaust gas. Additionally, an exhaust gas post-treatment apparatus 7 may be provided in the exhaust pipe 5 on the downstream side of the turbine 6 in terms of flow of the exhaust gas, and the introduction pipe 16 and the return pipe 17 may be connected to the exhaust pipe 5 on the upstream side of the exhaust gas post-treatment apparatus 7 in terms of flow of the exhaust gas. An open/close valve 19 may be provided in either one or both of the introduction pipe 16 and the return pipe 17.

Figure 7:
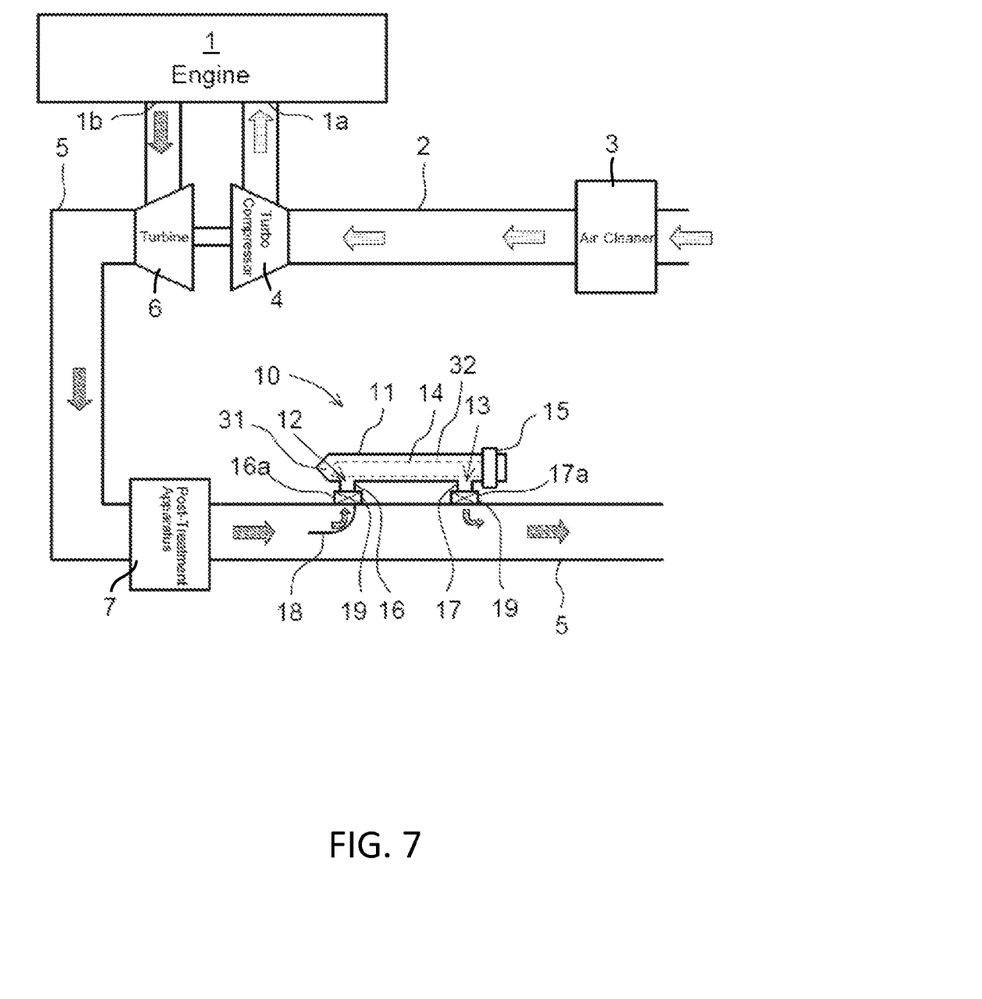
FIG. 7 is a schematic diagram showing an engine on which an exhaust sensor according to still another embodiment of the invention is mounted.

As shown in FIG. 7, a turbine 6 may be provided in the exhaust pipe 5, and the introduction pipe 16 and the return pipe 17 may be connected to the exhaust pipe 5 on the downstream side of the turbine 6 in terms of flow of the exhaust gas. Additionally, an exhaust gas post-treatment apparatus 7 may be provided in the exhaust pipe 5 on the downstream side of the turbine 6 in terms of flow of the exhaust gas, and the introduction pipe 16 and the return pipe 17 may be connected to the exhaust pipe 5 on the downstream side of the exhaust gas post-treatment apparatus 7 in terms of flow of the exhaust gas. An open/close valve 19 may be provided in either one or both of the introduction pipe 16 and the return pipe 17. Additionally, a guide 18 may be provided in the communication portion 16a between the exhaust pipe 5 and the introduction pipe 16 for the purpose of efficient introduction of the exhaust gas into the sensor body 11.

Figure 8:
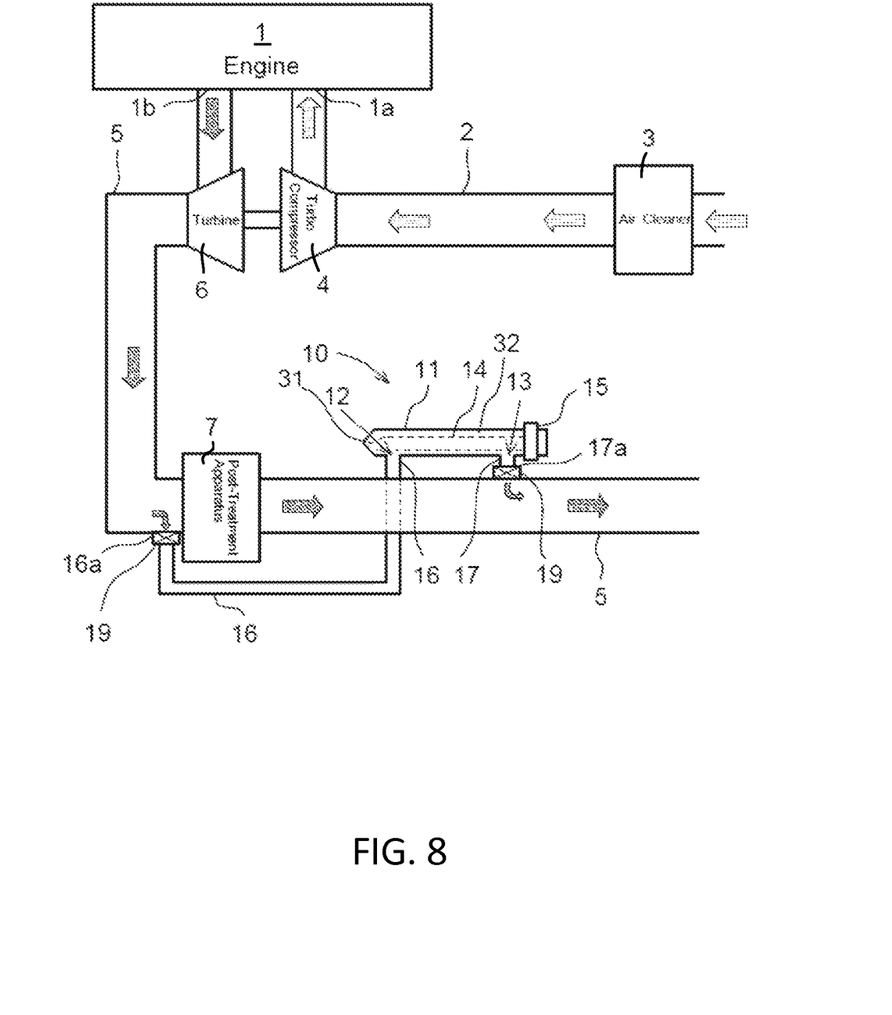
FIG. 8 is a schematic diagram showing an engine on which an exhaust sensor according to still another embodiment of the invention is mounted.

As shown in FIG. 8, a turbine 6 may be provided in the exhaust pipe 5, and the introduction pipe 16 and the return pipe 17 may be connected to the exhaust pipe 5 on the downstream side of the turbine 6 in terms of flow of the exhaust gas. Additionally, an exhaust gas post-treatment apparatus 7 may be provided in the exhaust pipe 5 on the downstream side of the turbine 6 in terms of flow of the exhaust gas, and the introduction pipe 16 may be connected to the exhaust pipe 5 on the upstream side of the exhaust gas post-treatment apparatus 7 in terms of flow of the exhaust gas, while the return pipe 17 may be connected to the exhaust pipe 5 on the downstream side of the exhaust gas post-treatment apparatus 7 in terms of flow of the exhaust gas. An open/close valve 19 may be provided in either one or both of the introduction pipe 16 and the return pipe 17.

Figure 9:
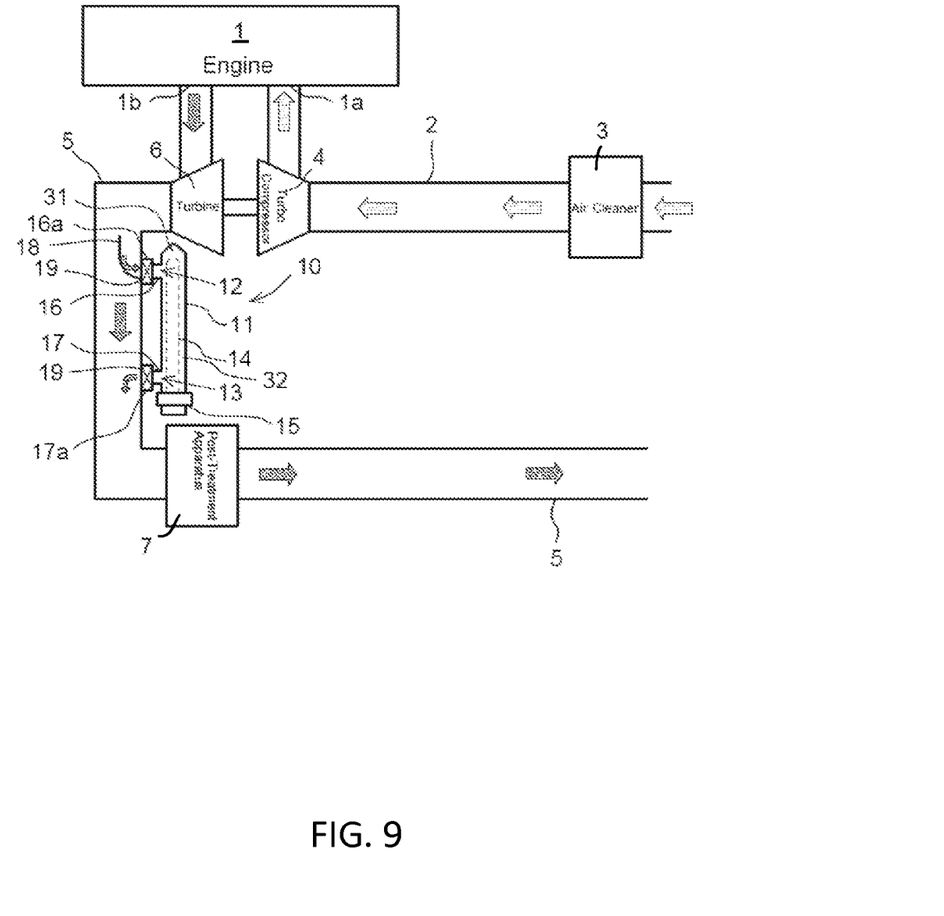
FIG. 9 is a schematic diagram showing an engine on which an exhaust sensor according to still another embodiment of the invention is mounted.

As shown in FIG. 9, a turbine 6 may be provided in the exhaust pipe 5, and the introduction pipe 16 and the return pipe 17 may be connected to the exhaust pipe 5 on the downstream side of the turbine 6 in terms of flow of the exhaust gas. Additionally, an exhaust gas post-treatment apparatus 7 may be provided in the exhaust pipe 5 on the downstream side of the turbine 6 in terms of flow of the exhaust gas, and the introduction pipe 16 and the return pipe 17 may be connected to the exhaust pipe 5 on the upstream side of the exhaust gas post-treatment apparatus 7 in terms of flow of the exhaust gas. An open/close valve 19 may be provided in either one or both of the introduction pipe 16 and the return pipe 17. Additionally, a guide 18 may be provided in the communication portion 16a between the exhaust pipe 5 and the introduction pipe 16 for the purpose of efficient introduction of the exhaust gas into the sensor body 11.

Figure 10:
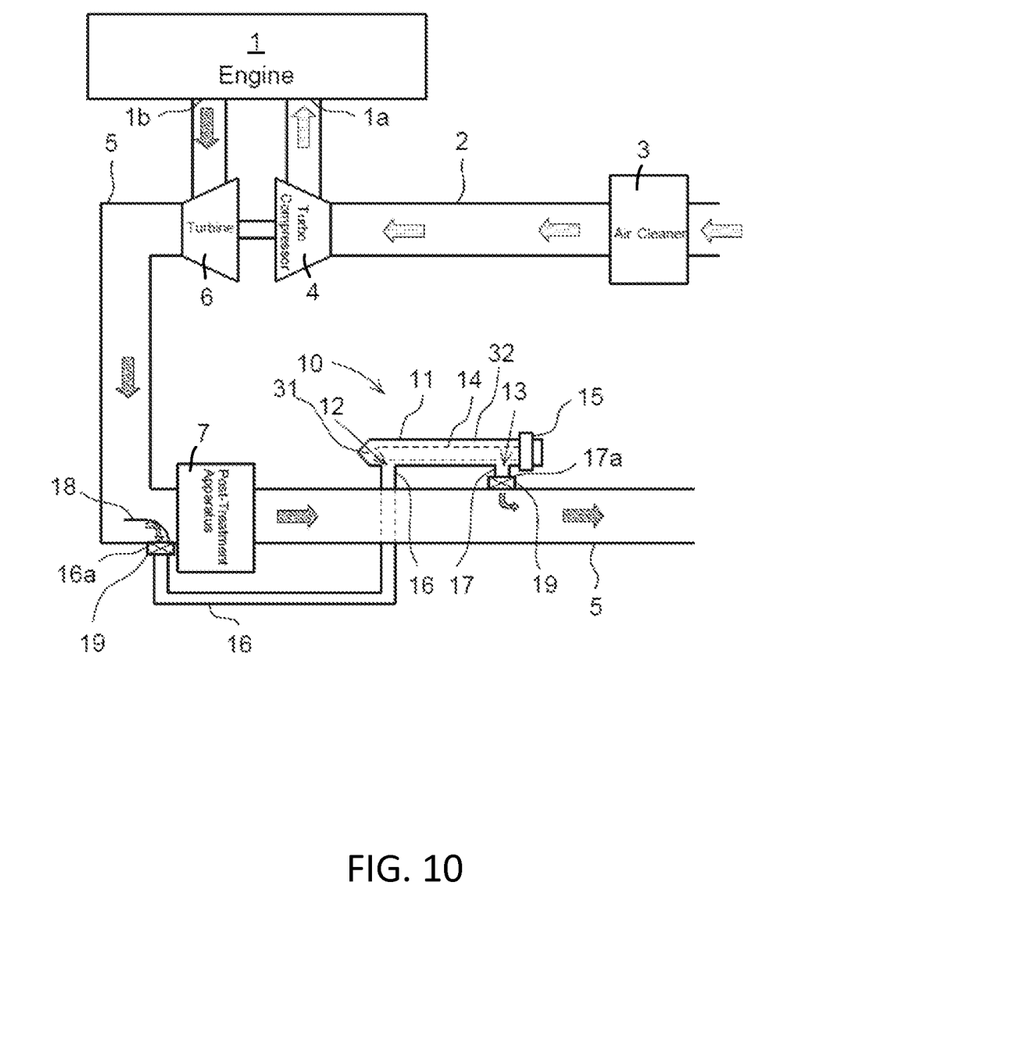
FIG. 10 is a schematic diagram showing an engine on which an exhaust sensor according to still another embodiment of the invention is mounted.

As shown in FIG. 10, a turbine 6 may be provided in the exhaust pipe 5, and the introduction pipe 16 and the return pipe 17 may be connected to the exhaust pipe 5 on the downstream side of the turbine 6 in terms of flow of the exhaust gas. Additionally, an exhaust gas post-treatment apparatus 7 may be provided in the exhaust pipe 5 on the downstream side of the turbine 6 in terms of flow of the exhaust gas, and the introduction pipe 16 may be connected to the exhaust pipe 5 on the upstream side of the exhaust gas post-treatment apparatus 7 in terms of flow of the exhaust gas, while the return pipe 17 may be connected to the exhaust pipe 5 on the downstream side of the exhaust gas post-treatment apparatus 7 in terms of flow of the exhaust gas. An open/close valve 19 may be provided in either one or both of the introduction pipe 16 and the return pipe 17. Additionally, a guide 18 may be provided in the communication portion 16a between the exhaust pipe 5 and the introduction pipe 16 for the purpose of efficient introduction of the exhaust gas into the sensor body 11.

The exhaust sensor 10 is not limited to a PM sensor, but may be any other sensor for measuring exhaust gas components other than PM.

Although the invention above has been described in connection with preferred embodiments of the invention, it will be evident for a person skilled in the art that several modifications are conceivable without departing from the invention as defined by the following claims.

What is claimed is:

1. A particulate matters (PM) sensor arranged outside of an exhaust pipe of an engine and measuring a quantity of PM within exhaust gas based on a variation in electrical charge, the PM sensor comprising:
   a cylindrical sensor body having both ends closed;
   a gas inlet formed at one end of the sensor body and communicating with the exhaust pipe through an introduction pipe;
   a gas outlet formed at the other end of the sensor body and communicating, through a return pipe, with the exhaust pipe on a downstream side of the introduction pipe in terms of flow of the exhaust gas;
   a nozzle arranged concentrically with the cylindrical sensor body and ejecting air from the front end thereof;
   an electrode for electrically charging air ejected from the nozzle; and
   an ion trap trapping the PM;
   wherein an open/close valve is provided in both of the introduction pipe and the return pipe.

2. The PM sensor according to claim 1, wherein a turbine is provided in the exhaust pipe, and the introduction pipe and the return pipe are connected to the exhaust pipe on the downstream side of the turbine in terms of flow of the exhaust gas.

3. The PM sensor according to claim 2, wherein an exhaust gas post-treatment apparatus is provided in the exhaust pipe on the downstream side of the turbine in terms of flow of the exhaust gas, and the introduction pipe and the return pipe are connected to the exhaust pipe on the downstream side of the exhaust gas post-treatment apparatus in terms of flow of the exhaust gas.

4. The PM sensor according to claim 3, wherein a guide is provided in the communication portion between the exhaust pipe and the introduction pipe for the purpose of efficient introduction of the exhaust gas into the sensor body.

5. The PM sensor according to claim 2, wherein an exhaust gas post-treatment apparatus is provided in the exhaust pipe on the downstream side of the turbine in terms of flow of the exhaust gas, and the introduction pipe and the return pipe are connected to the exhaust pipe on the upstream side of the exhaust gas post-treatment apparatus in terms of flow of the exhaust gas.

6. The PM sensor according to claim 5, wherein a guide is provided in the communication portion between the exhaust pipe and the introduction pipe for the purpose of efficient introduction of the exhaust gas into the sensor body.

7. The PM sensor according to claim 2, wherein an exhaust gas post-treatment apparatus is provided in the exhaust pipe on the downstream side of the turbine in terms of flow of the exhaust gas, and the introduction pipe is connected to the exhaust pipe on the upstream side of the exhaust gas post-treatment apparatus in terms of flow of the exhaust gas, while the return pipe is connected to the exhaust pipe on the downstream side of the exhaust gas post-treatment apparatus in terms of flow of the exhaust gas.

8. The PM sensor according to claim 7, wherein a guide is provided in the communication portion between the exhaust pipe and the introduction pipe for the purpose of efficient introduction of the exhaust gas into the sensor body.

9. The PM sensor according to claim 2, wherein a guide is provided in the communication portion between the exhaust pipe and the introduction pipe for the purpose of efficient introduction of the exhaust gas into the sensor body.

10. The PM sensor according to claim 1, wherein a guide is provided in the communication portion between the exhaust pipe and the introduction pipe for the purpose of efficient introduction of the exhaust gas into the sensor body.

* * * * *